United States Patent [19]

Chin

[11] Patent Number: 5,613,947
[45] Date of Patent: Mar. 25, 1997

[54] EVERTING CANNULA APPARATUS AND METHOD

[75] Inventor: Albert K. Chin, Palo Alto, Calif.

[73] Assignee: Origin Medsystems, Inc., Menlo Park, Calif.

[21] Appl. No.: 558,759

[22] Filed: Nov. 15, 1995

Related U.S. Application Data

[63] Continuation of Ser. No. 269,666, Jul. 1, 1994, abandoned.

[51] Int. Cl.$^6$ .................................................. A61M 29/00
[52] U.S. Cl. ............................ 604/96; 604/271; 604/49; 606/194
[58] Field of Search .................... 604/49, 51, 54, 604/55, 96, 271; 606/192, 194

[56] References Cited

U.S. PATENT DOCUMENTS

| | | | |
|---|---|---|---|
| 3,500,819 | 3/1970 | Silverman | 604/271 |
| 4,271,839 | 6/1981 | Fogarty et al. | 604/271 |
| 4,775,362 | 10/1988 | Kronner | 604/55 |
| 4,863,440 | 9/1989 | Chin | 604/271 |
| 5,300,023 | 4/1994 | Lowery et al. | 604/271 |
| 5,309,896 | 5/1994 | Moll et al. | 128/20 |
| 5,364,345 | 11/1994 | Lowery et al. | 604/55 |
| 5,437,638 | 8/1995 | Bowman | 604/271 |

OTHER PUBLICATIONS

Session II, Advances in Peripheral Techniques I—Endoluminal Grafts, International Congress VII, Endovascular Interventions, On the Cutting Edge, Feb. 14, 1994.
Session IX, Advances in Peripheral Techniques II—Aneurysm Exclusion and Intraluminal Bypass, International Congress VII, Endovascular Interventions, On the Cutting Edge, Feb. 17, 1994.
"Blunt Tip Trocar and Sleeve", Origin Medsystems, Inc., Menlo Park, California, Oct. 1992.
D.C. Brewster, "Vascular Surgery: Principles and Technique", Appleton & Lange, 1989, pp. 237–250, 461–466.

*Primary Examiner*—John D. Yasko
*Attorney, Agent, or Firm*—Albert C. Smith

[57] ABSTRACT

A double-lumen balloon cannula and method for performing blunt dissection of an elongated, non-spherical cavity under visual control includes a tubular lumen to slidably support an endoscope therewithin, and a second lumen having an inverted, nonelastomeric, transparent balloon attached at one end and contained therewithin that is capable of being everted in response to fluid under pressure applied thereto. The endoscope is selectively advanced within the everting balloon to visualize tissue in the elongated cavity through the balloon.

9 Claims, 6 Drawing Sheets

EVERTING CANNULA APPARATUS AND METHOD

This is a continuation of application Ser. No. 08/269,666 filed on Jul. 1, 1994, now abandoned.

BACKGROUND OF THE INVENTION

1. Field of the Invention

The present invention relates generally to dissection cannula used for forming an elongated cavity in tissue planes. The present invention relates specifically to an everting balloon dissection cannula.

2. Description of Background Art

Present methods for the formation of an elongated cavity involve the use of blunt probes that are pushed through body tissue to accomplish the dissection. The force exerted by the passage of mechanical probes may lead to blood vessel avulsion and trauma to tissue and internal organs. A method of atraumatic blunt dissection is desired, preferably a method of accomplishing this blunt dissection under visual control.

Several balloon catheters are disclosed in various issued patents and publications. Exemplary everting balloon catheters used for arterial dilation include U.S. Pat. No. 4,271,839 (Fogarty et al., Jun. 6, 1981), U.S. Pat. No. 4,479,497 (Fogarty et al., Oct. 10, 1984), U.S. Pat. No. 4,863,440 (Chin, Sep. 5, 1989), and U.S. Pat. No. 4,526,175 (Chin et al., Jul. 7, 1985).

Single lumen everting balloon catheters, such as that disclosed in the Fogarty et al. '839 patent, do not provide a channel for an endoscope. Even if an endoscope were inserted into the disclosed single balloon lumen, the endoscope would be unable to track down to the distal part of the catheter due to the presence of the balloon positioned at the end of the catheter. In such a construction, structures lying outside of the balloon would be outside the range of view for that endoscope. The folds of balloon lying within the catheter, as disclosed in the Fogarty et al. '839 patent, do not provide an optically clear viewing window, as multiple layers of transparent balloon material distort possible imaging. A single layer of balloon material is needed for successful visualization.

Double lumen everting balloon catheters, such as those disclosed in the Fogarty et al. '497 and the Chin '440 patents, have a through-lumen 102 that permits the passage of an endoscope 100. However, an endoscope 100 used in conjunction with those disclosed catheters is unable to monitor the dissection process, since the endoscope 100 lies within the central lumen 106 proximal to the everting balloon 104, as illustrated in FIG. 1A. As the balloon 104 everts from the catheter, the internal inflation pressure squeezes the walls of the balloon and closes off the distal viewing channel 108, as illustrated in FIG. 1B. Also, the area that requires monitoring during balloon dissection is located at the advancing front of the everting balloon 104. This area corresponds to the balloon/tissue interface subject to forces that cause tissue separation. Thus, an endoscope 100 in the central lumen 106 of existing double lumen everting balloon catheters is unable to view the tissue separation area, since a double layer of balloon membrane lies between the endoscope 100 and the tissue blocking the endoscopic line of sight 110, as illustrated in FIG. 1C. This double layer obscures and distorts the viewing image.

The catheter disclosed in the Chin et al. '175 patent has a looped lumen which does not accommodate a rigid endoscope. A balloon cannula has been tested which performs blunt dissection using a long, tubular, generally inelastic balloon that is rolled up outside the lumen. As illustrated in FIGS. 2A and 2B, the rolled up balloon 104 is introduced to the tissue cavity 112. As the balloon 104 is inflated and unrolled, as shown in FIG. 2B, it remains partially folded as it inflates, forming a generally spherical cavity 112. This spherical cavity 112 is contrasted with the desired elongated cavity 114.

Other versions of balloon dissection cannulae are commercially available, for example, from Origin Medsystems, Inc., the assignee herein. One such version uses a spherical, elastomeric balloon, and another such version uses a generally elliptical, inelastic balloon that is rolled up outside the lumen. These cannulae dissect generally spherical cavities.

SUMMARY OF THE INVENTION

The present invention is a double-lumen balloon cannula that performs blunt dissection of an elongate, non-spherical cavity under visual control. The cannula includes a circular lumen that accommodates an endoscope therewithin, and a second lumen having an inverted, nonelastomeric, transparent balloon contained therewithin and attached at one end to the outer, proximal end of the second lumen and at the other end to the outer, proximal end of the first lumen. Thus, when the balloon is everted, it extends over the distal end of both lumen to permit passage therethrough of the endoscope for visualization of the tissue adjacent the balloon.

Specifically, the dissection cannula of the present invention includes a multi-lumen cannula, preferably a double lumen cannula, with an elongated nonelastomeric balloon attached to the distal end of the cannula such that the balloon extends across the distal end of both lumen when the balloon is in an active, everted state. One lumen of the cannula accommodates a 10 mm diameter endoscope. A second lumen contains an inverted balloon. Upon pressurization of the cannula, the balloon everts from the cannula, dissecting a tunnel in the subject tissue. The endoscope may be extended from the first lumen to reside in the everted portion of the balloon to monitor the progress of the dissection through the transparent wall of the balloon.

A method also is disclosed for dissecting an elongate cavity using the inventive cannula of the present invention. The method includes the steps of: bluntly dissecting to reach the target tissue; inserting the dissection cannula with an everting balloon of the type described above; and then inflating the balloon to dissect an elongated cavity, while observing the dissection process via the endoscope that can be advanced within the balloon. The method further may include deflating the balloon and removing the dissection cannula, then maintaining the dissection cavity using insufflated gas through a balloon cannula that seals the incision against gas leakage.

In an alternative method, the dissected cavity may be maintained using a system of mechanical retractors. A fan retractor may be inserted through the incision and connected to a lifting arm to support the ceiling of the cavity, while a separate retractor may be introduced through the same or separate incision to displace the side of the cavity. In combination, the ceiling and side retractors provide maintenance of the cavity in the same manner as gas insufflation.

The cannula of the present invention may be used to dissect an elongated cavity adjacent to the abdominal aorta, isolating the aorta in preparation for aortic graft placement. The cannula also may be used to form an elongated cavity adjacent to the femoral artery, extending under the inguinal ligament and continuing adjacent to the iliac artery. This cavity may be used to pass the femoral limb of an aortobifemoral graft from the retroperitoneum to the groin region for the distal femoral anastomosis. The cannula also may be used to form elongated cavities in other tissue planes; for example, an elongated subcutaneous tunnel may be formed along the abdominal and chest wall, for passage of cardiac pacemaker leads or indwelling central venous lines.

DETAILED DESCRIPTION OF THE PREFERRED EMBODIMENTS

In accordance with one embodiment of the present invention, a blunt dissection cannula includes a dissection balloon and an endoscope for visually monitoring the dissection. The present invention also includes a method for such blunt dissection.

Figure 1A:
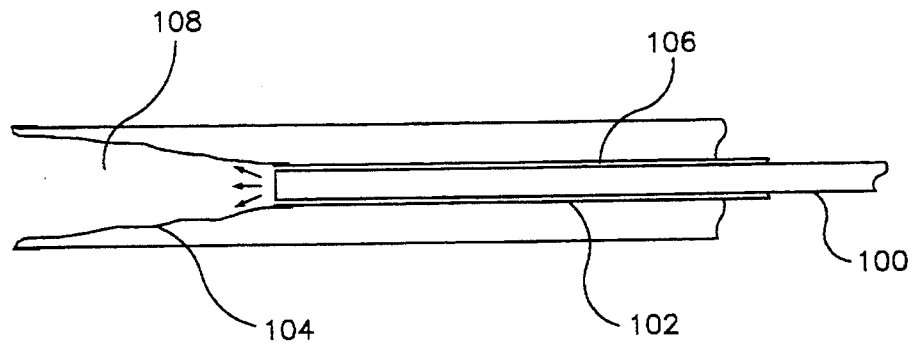
FIGS. 1A–1C show cross-sections of a cannula of the prior art.
Figure 1B:
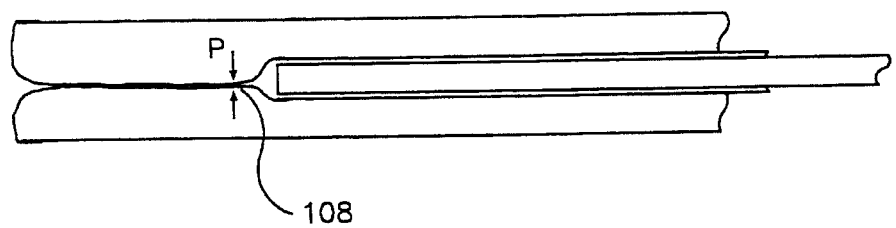
Figure 1C:
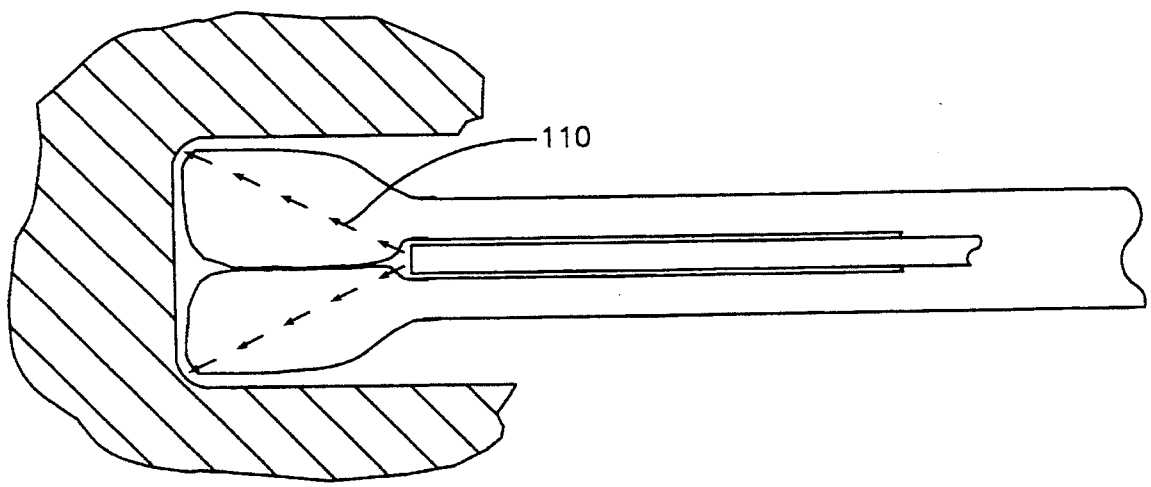
Figure 2A:
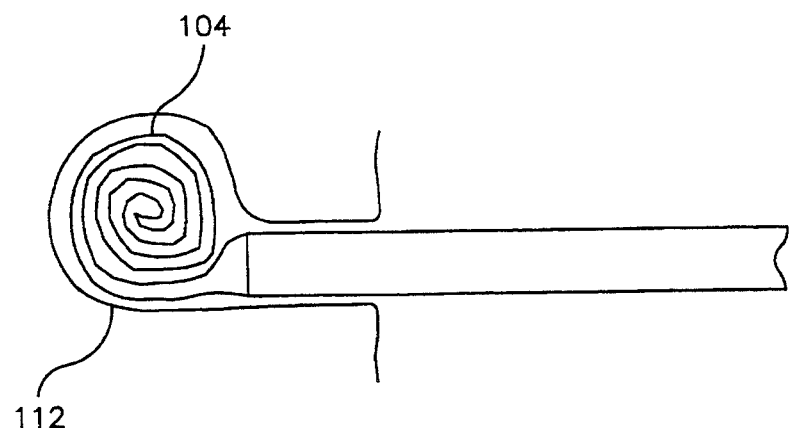
FIGS. 2A–2B show cross-sections of another cannula of the prior art.
Figure 2B:
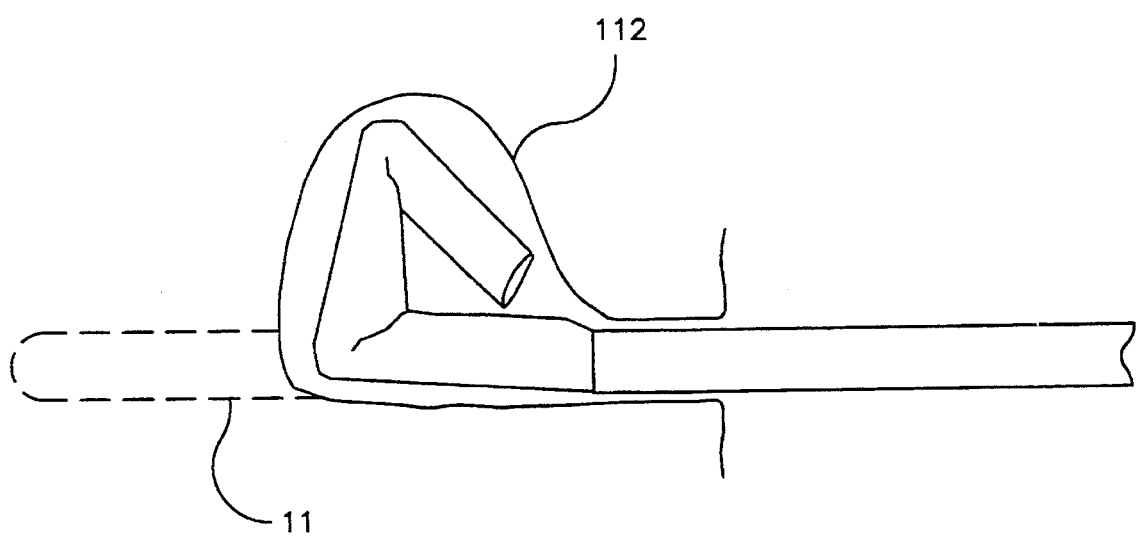
Figure 3A:
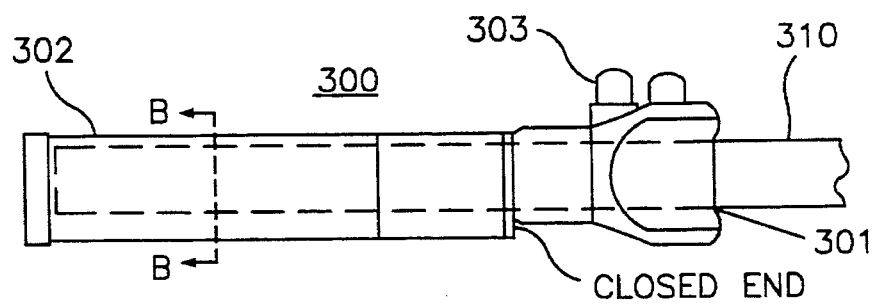
FIG. 3A shows a side elevation view of an embodiment of the cannula of the present invention.
Figure 3B:
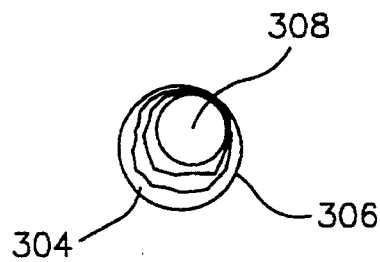
FIG. 3B shows in cross-section the cannula of FIG. 3A taken along lines B—B of that figure.

FIG. 3A shows an embodiment of the dissection cannula 300 of the present invention. That cannula 300 includes an elongate, tubular member 302 having one lumen 304 for containing an inverted balloon 306 and another lumen 308 for supporting an endoscope 310 therein as shown in cross-section in FIGS. 3B and 3C. In other embodiments, the cannula 300 may include additional lumens, such as a lumen through which a guide-wire may be passed.

The cannula 300 may be manufactured from a variety of bioinert, substantially inelastic material. Preferred materials include polyethylene, polyurethane, polyvinyl chloride, polyimide plastic, and the like, preferably material having a tensile strength of at least 10,000 psi. Preferably, each lumen of the cannula has a wall thickness of between about 0.001 inch and 0.003 inch.

An elliptical, nonelastic balloon 306 is inverted into lumen 304 prior to introduction of the cannula 300 to the dissection site. The balloon 306 is attached to the outer edges of the distal end of the cannula 300 to ensure that the balloon 306, when in its everted, inflated state (shown in FIG. 3D), extends outwardly from the distal end of the cannula 300 and completely encloses that end of the cannula 300. In its inverted state (shown in longitudinal cross-section in FIG. 3C), the balloon 306 is rolled up or otherwise fitted into the balloon lumen 304. With the balloon 306 in the illustrated inactive, inverted state, the cannula 300 may be introduced into the dissection site.

The balloon 306 for the present cannula 300 may be formed from any appropriate bioinert, flexible, inelastic material, such as polyethylene, polyester, or the like. The balloon 306 has an elliptical shape in side view when extended to form an elongated cavity 312 upon activation and introduction of the cannula 300 into the target dissection site. A preferred cavity length to cavity diameter formed by the cannula 300 with the extended balloon 306 is about 4:1, or greater. Such an elongated cavity 312 is useful, for example, to facilitate endoscopic retroperitoneal aortobifemoral bypass graft placement.

Figure 3D:
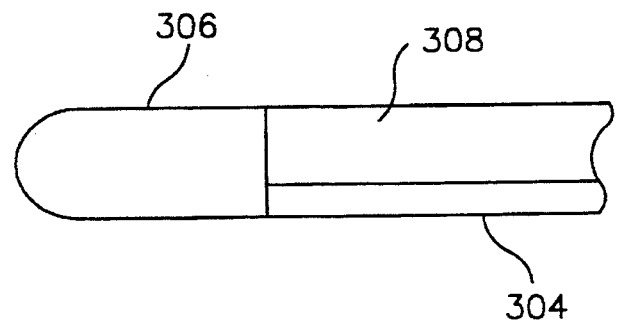
FIG. 3D is a longitudinal cross-section of the cannula of FIG. 3C, showing the balloon in its active, everted position.
Figure 3C:
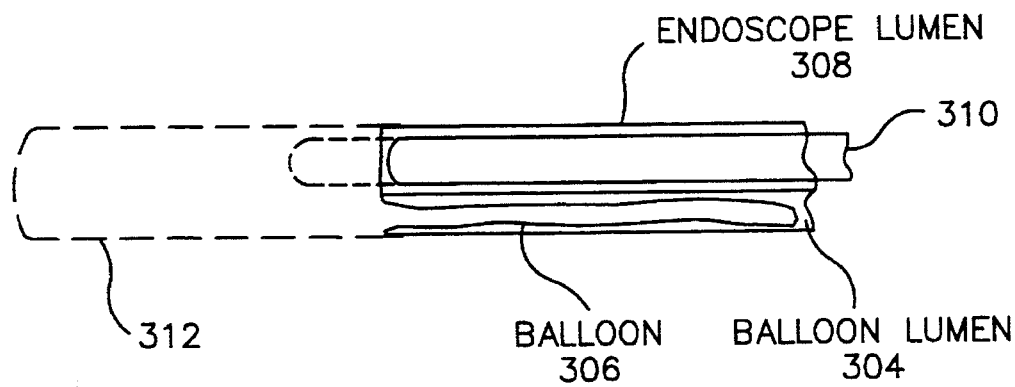
FIG. 3C shows the cannula of FIG. 3A in longitudinal cross-section, showing the balloon in its inactive, inverted position within the balloon lumen.

As shown in FIG. 3A, the proximal end of the cannula 300 preferably is sealed. In addition, a conventional sliding pressure seal 301 is provided around an endoscope inserted into the lumen 308. This enables a positive pressure to be established within the balloon lumen 304 upon activation of the cannula 300 at the dissection site. When a positive pressure is established within that lumen 304, the inverted balloon shown in FIG. 3C becomes everted and extended, as shown in FIG. 3D. The positive pressure necessary to evert the balloon 306 may be produced by air or other fluid introduced into the lumen 304 via a pressure fitting 303 at the proximal end of the cannula 300 which communicates with the balloon lumen 304 to receive a source of air or other fluid under pressure, for example from a manually operable syringe.

The present cannula 300 also includes a second lumen 308 for housing an endoscope 310 therewithin. The size of the lumen 308 depends on the diameter of the endoscope 310 to be introduced therewithin. A preferred endoscope 310 having a tubular diameter of about 10 mm is commercially available from Karl Storz Endoscopy America, Inc., Culver City, Calif. However, other commercially available endoscopes 310 that may be used in practicing the present invention include those which are as small as 1.00 to 1.75 mm in diameter.

Providing a separate lumen for an endoscope 310 permits the endoscope 310 to be advanced to the distal end of the cannula 300 for visualization from within the everting balloon 306 during dissection. This facilitates extending the endoscope 310 beyond the distal end of the cannula 300 when the balloon 306 is in its partially everted state for more clear viewing through the balloon 306 of the surrounding tissue. Visualization through the transparent wall of the inverted balloon 306 is particularly useful during initial placement of the cannula 300 to ensure that the cannula 300 lies in the proper plane prior to balloon eversion. For example, muscle planes have a red appearance, while retroperitoneal planes contain fat and have a yellow appearance. If the cannula 300 is advanced into the abdominal cavity, bowel will be visualized by the endoscope 310.

In operation, as the cannula 300 is pressurized, the balloon 306 everts from the distal end of the cannula 300, separating tissue planes as it proceeds through the adjacent tissue. The endoscope 310 may be advanced forward within the everting balloon 306 while maintaining pressurization via the sliding seal 301 to promote continuous viewing through a single layer of balloon material. The proximal end of the cannula 300 is closed off, and a sliding seal 301 at the proximal end of the endoscopic lumen 308 seals that lumen 308 against the sliding movement therein of the endoscope 310.

Figure 4:
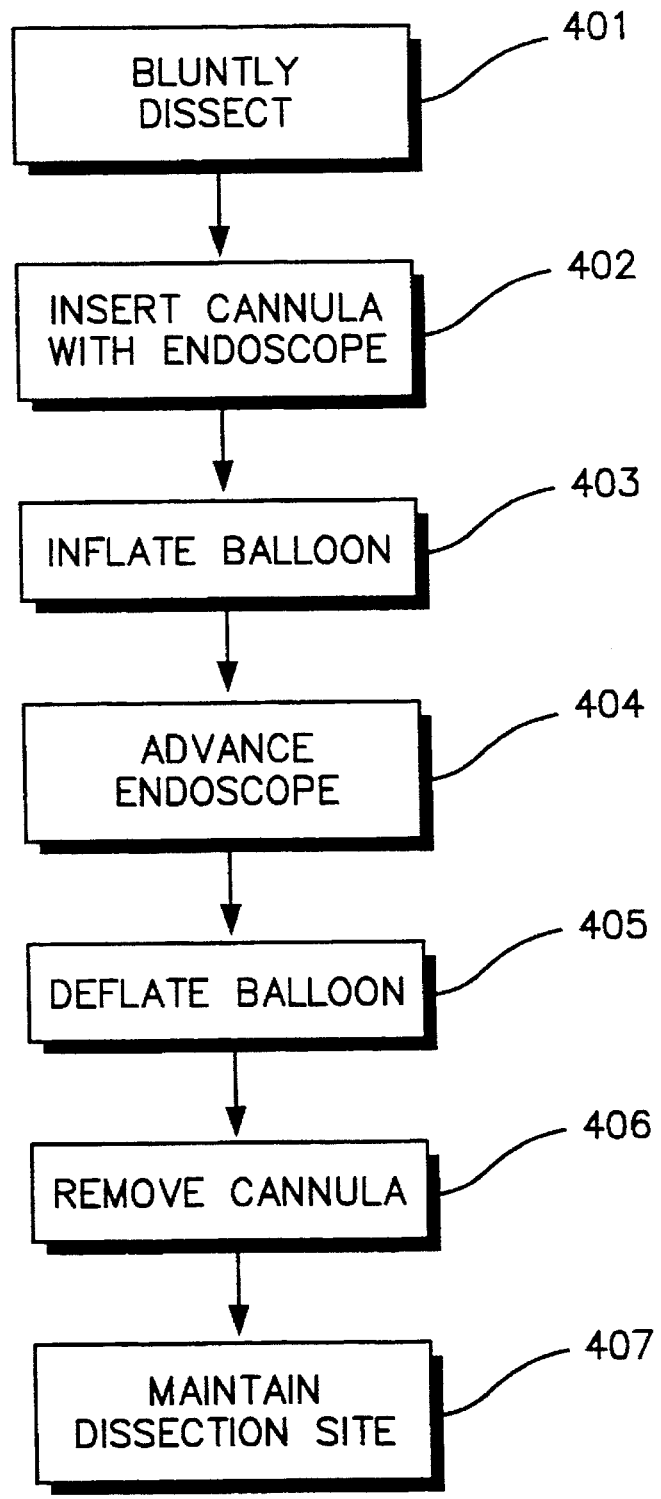
FIG. 4 is a flowchart of one embodiment of the method of the present invention.

The method for dissecting an elongated cavity using the cannula of the present invention is shown in the flow diagram of FIG. 4. The method includes the steps of bluntly dissecting 401 to reach the target tissue and then inserting 402 the dissection cannula 300 with an everting balloon 306 as described above. The balloon 306 then is inflated 403 to dissect an elongated cavity 312, for example, adjacent to the abdominal aorta. The endoscope 310 then may be advanced 404 forward to permit a user to observe the dissection process. The method then includes deflating 405 the balloon 306 and removing 406 the dissection cannula 300, and then maintaining 407 the dissection cavity 312, for example, using insufflated gas in a conventional manner such that a seal forms at the incision and pressurizes the dissected cavity 312.

Figure 5:
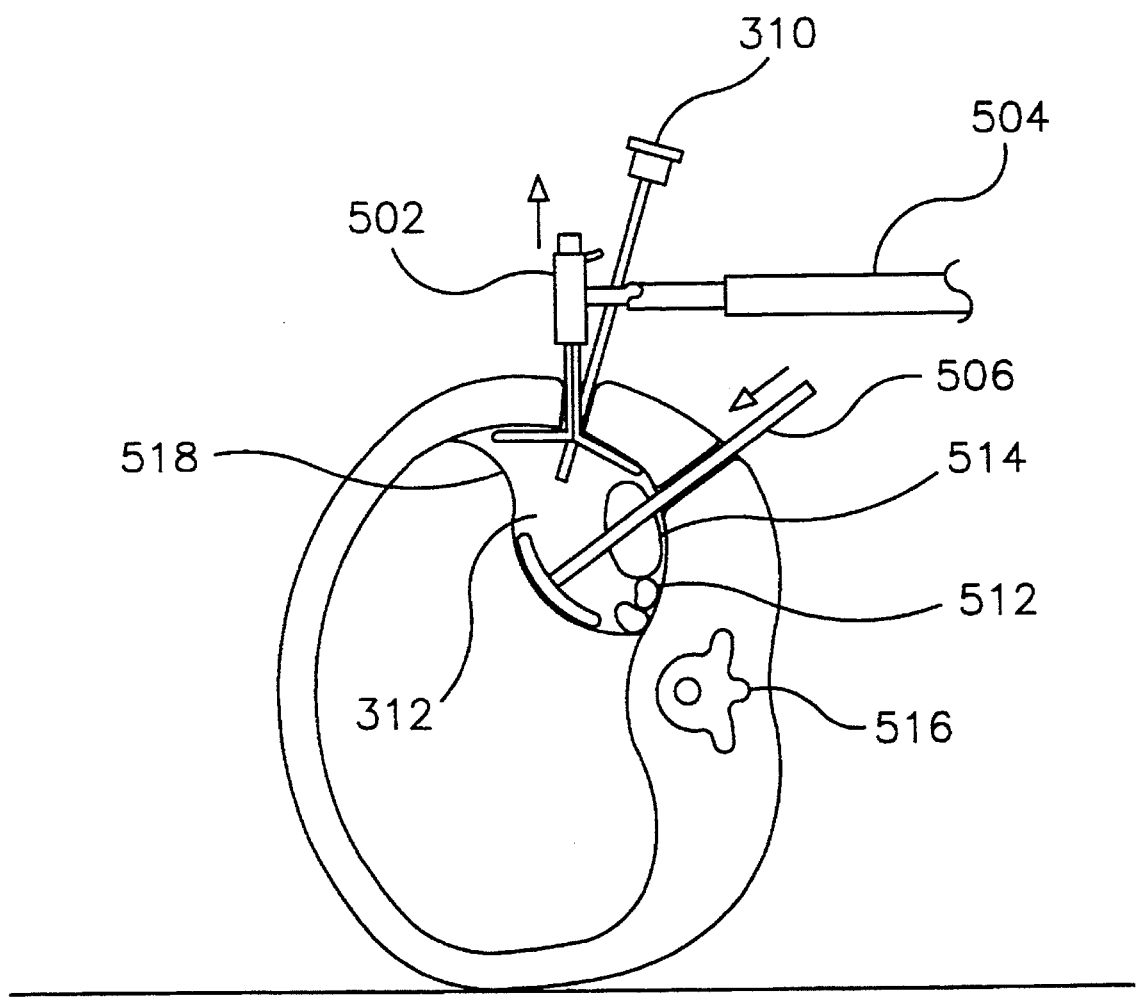
FIG. 5 is an end-section view of a passageway formed by the present invention and maintained using a mechanical retractor device.

Alternatively, an inflatable structural balloon or mechanical structure may be used to support the dissected cavity 312. For example, the cavity 312 may be maintained by mechanical retraction or by a mechanical fan retractor 502 attached to a powered lifting arm 504 plus a separate flat balloon retractor 506 used to displace the side wall of the cavity, as shown in FIG. 5. In that illustrated embodiment, the cavity 312 is formed adjacent to the aorta 512 and kidney 514. Also shown are the spine 516 and the retracted peritoneum 518. In that illustrated embodiment, the endoscope 310 may be introduced behind the legs of the fan retractor 502 that connect to the mechanical lifting arm 504. An exemplary structural balloon that may be used in practicing the present invention is shown in U.S. Pat. No. 5,309,896.

The proximal anastomosis of a graft then may be sewn into the aorta within the dissected cavity to secure the graft in place. Bilateral groin incisions may be made to isolate the femoral vessels and the everting balloon dissection cannula 300 may be used to dissect tunnels from both groins back to the retroperitoneal aortic cavity. The femoral limbs of the graft then may be pulled out through the two groin tunnels to perform distal anastomoses.

In further detail, the method described above may include making a small flank incision and carrying the incision down to muscle before bluntly dissecting 401 and spreading the muscle apart to reach the retroperitoneal space lying directly outside of the peritoneum. A specialized everting balloon dissection cannula 300, of the type described herein and with a removably incorporated endoscope, may be inserted 402 into the retroperitoneal space. The dissection balloon 306 is inflated 403 to dissect an elongated cavity adjacent to the abdominal aorta. The balloon 306 is deflated 405 and the dissection cannula 300 is removed 406, maintaining 407 the dissection cavity, using insufflated gas through a balloon cannula that seals the incision against gas leakage.

The present cannula 300 herein described may be used in techniques for performing aortofemoral bypass grafting that are less invasive than presently practiced techniques. For example, the everting cannula 300 may be used to dissect a passageway along the aorta to isolate the aorta for aortobifemoral bypass grafting. The cannula 300 may be used to dissect a passageway adjacent to and extending from the femoral artery, under the inguinal ligament to the iliac artery and to the aorta. Such a passageway may be used to pass the femoral limb of an aortobifemoral graft from the retroperitoneum to the groin region for the distal femoral anastomosis.

Figure 6:
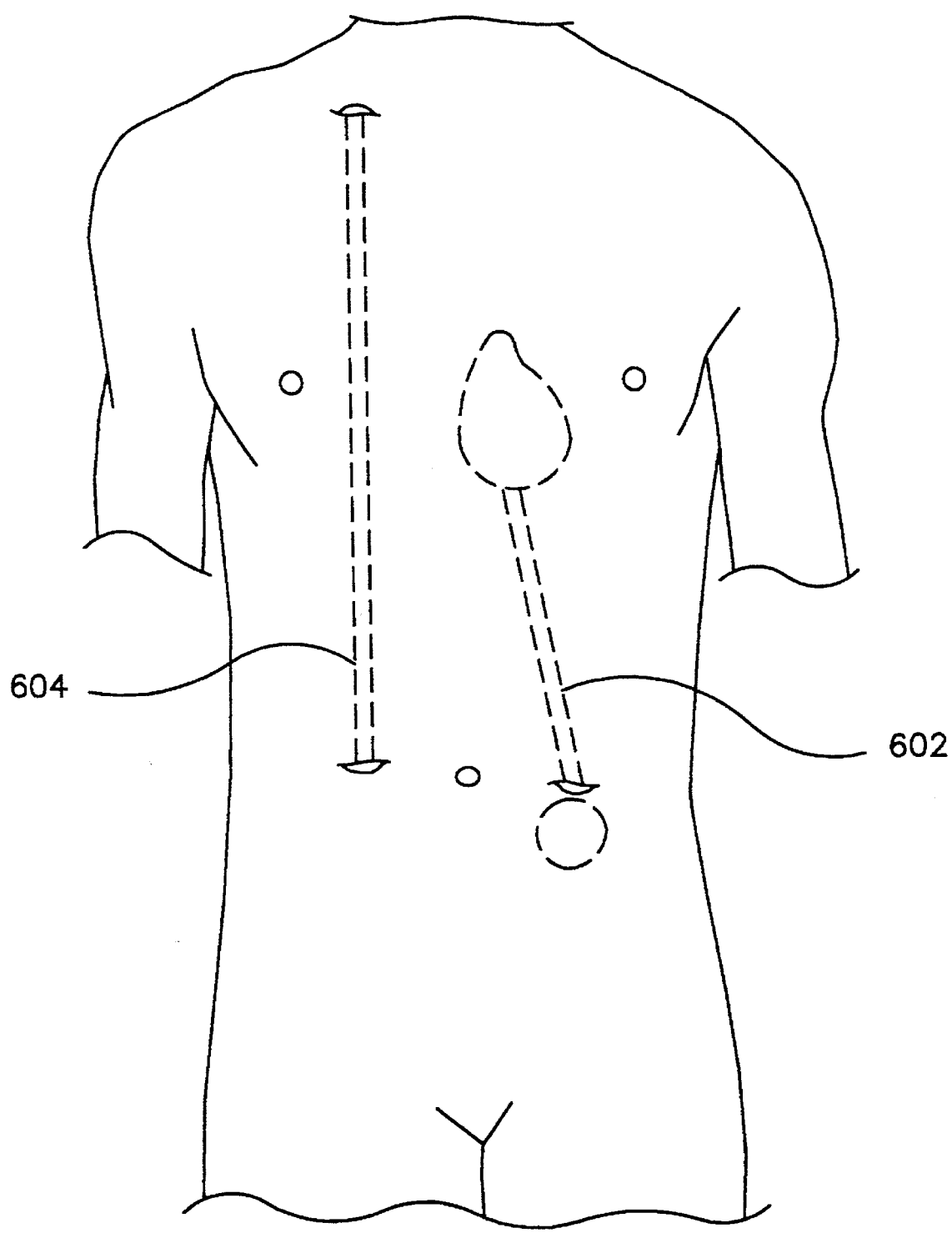
FIG. 6 shows exemplary locations for subcutaneous tunnels formed by the present invention.

Alternatively, the cannula 300 may be used to create a passageway along the anterior abdominal and chest wall to pass in-dwelling central venous catheters such as the Hickman and Broviac catheters. The cannula 300 also may be used to create a passageway 602, as shown in FIG. 6, pass battery lead wires connecting the battery in the abdominal wall with the cardiac pacemaker. The location of a passageway 604 that may be formed using the present cannula 300 for a central venous catheter also is shown.

What is claimed is:

1. A balloon dissection cannula for dissecting an elongated cavity in tissue planes, comprising:

an elongated tube element having a proximal closed end and a distal end and, including an inner tube element disposed within the elongated tube element along a portion of the length thereof to form a plurality of lumens within the elongated tube element;

an inverted balloon having a flexible wall in fluid-tight attachment to the elongated tube element and disposed in a first one of the lumens formed between the elongated tube element and the inner tube element and capable of being everted in response to fluid under pressure applied thereto, for positioning at a predetermined location within a passageway in tissue planes to dissect the elongated cavity in tissue planes distal to the elongated tube element; and the inner tube element forming a second one of the lumens disposed to receive an endoscope in fluid-tight engagement within the inner tube element for visualizing from within and through the balloon wall the tissue in the elongated cavity as the balloon is everted in response to fluid under pressure applied thereto, with an endoscope within the second lumen being exposed to said balloon-everting fluid under pressure.

2. The cannula of claim 1, wherein the balloon is non-elastomeric and substantially transparent.

3. The cannula of claim 1, wherein the balloon is attached to the distal end of the cannula to form a fluid-tight seal therewith.

4. The cannula of claim 1, wherein the second lumen comprises a diameter in the range of between about 1 and about 10 millimeters for receiving an endoscope in slidable relationship therein.

5. A method for blunt dissection and separation of adjacent tissue planes using a balloon dissection cannula that includes an elongated tube element, including a plurality of lumens, having a proximal closed end and a distal end, and an inverted dissection balloon having a flexible wall and being positioned in a first one of the lumen, that is capable of being everted in response to fluid under pressure applied thereto while positioned at a predetermined location within a passageway in tissue planes to dissect an elongated cavity in tissue planes distal to the tube element, and including an endoscope positioned within a second one of the lumen that is disposed within the first one of the lumen, for visualizing the cavity through the balloon wall while the balloon is everting, the method comprising the steps of:

forming an incision in tissue extending to a selected tissue plane;

spreading the incision and underlying tissue to form a space in the selected tissue plane;

introducing the cannula through the incision into the space;

inflating the dissection balloon within the space to dissect the tissue plane to create an elongated cavity in the tissue planes; and selectively advancing the endoscope slidably within the second lumen for visualizing tissue from within and through the wall of the everted balloon within the elongated cavity.

6. The method of claim 5, further comprising the steps, after the inflating step, of retractably sliding the endoscope within the second lumen; and deflating the dissecting balloon and removing the dissection cannula.

7. The method of claim 6, further comprising the step of, after deflating the dissecting balloon, maintaining the dissected cavity.

8. The method of claim 7, wherein the step of maintaining the dissected cavity comprises using one from the group consisting of: insufflated gas, a structural balloon, and mechanical structural support.

9. A balloon dissection cannula for dissecting an elongated cavity in tissue planes, comprising:

an elongated tube element, including a plurality of lumens having a proximal closed end and a distal end;

an inverted balloon of flexible, substantially transparent material disposed in a first one of the lumens and capable of being everted in response to fluid under pressure applied thereto, for positioning at a predetermined location within a passageway to dissect the elongated cavity in tissue planes distal to the tube element; and a second one of the lumens disposed within the first one of the lumens to receive an endoscope in fluid-tight engagement within the second lumen for visualizing through the substantially transparent material of the balloon wall the tissue in the elongated cavity as the balloon is everted in response to fluid under pressure applied thereto, with an endoscope within the second lumen being exposed to said balloon-everting fluid under pressure.

* * * * *